United States Patent [19]

Toseland et al.

[11] Patent Number: 4,482,769
[45] Date of Patent: Nov. 13, 1984

[54] REDUCING 2,4-DINITROORTHO-CRESOL IN EFFLUENT STREAM FROM DINITROTOLUENE PROCESS

[75] Inventors: Bernard A. Toseland; Richard Van Court Carr, both of Allentown, Pa.

[73] Assignee: Air Products and Chemicals, Inc., Allentown, Pa.

[21] Appl. No.: 533,166

[22] Filed: Sep. 16, 1983

[51] Int. Cl.³ .............................................. C07C 79/10
[52] U.S. Cl. ................................................. 568/934
[58] Field of Search ....................................... 568/934

[56] References Cited

U.S. PATENT DOCUMENTS 4,224,249  9/1980  Kunz et al. ........................ 260/580
4,361,712  11/1982  Herman ............................. 568/934

FOREIGN PATENT DOCUMENTS 1031450  6/1966  United Kingdom .

Primary Examiner—Leland A. Sebastian
Attorney, Agent, or Firm—Russell L. Brewer; E. Eugene Innis; James C. Simmons

[57] ABSTRACT

Dinitrotoluene, which is produced by mixed acid nitration of toluene, is purified in a way which produces a product suitable for conversion to toluene diamine and a less environmentally objectionable by-product stream. The process involves contacting a crude dinitrotoluene stream containing by-product nitrophenolic materials with an alkaline material and monitoring the pH such that dinitroorthocresol by-product is maintained in the organic phase while the trinitroorthocresol by-products are converted to water-soluble materials and removed with an aqueous phase.

6 Claims, 2 Drawing Figures

4,482,769

REDUCING 2,4-DINITROORTHO-CRESOL IN EFFLUENT STREAM FROM DINITROTOLUENE PROCESS

TECHNICAL FIELD

This invention pertains to selective purification of dinitrotoluene produced by the mixed acid technique in the nitration of toluene.

DESCRIPTION OF THE PRIOR ART

Commercially, dinitrotoluene is produced by the mixed acid nitration of toluene, the mixed acid being a mixture of concentrated sulfuric and nitric acids. In this type of process, toluene is first nitrated to form mononitrotoluene, the mononitrotoluene then being separated from the aqueous phase formed in the first nitration stage and dinitrated with fresh acid in a second nitration stage. The dinitrotoluene product then is recovered from the dinitration reactor and the impurities present in the system, e.g. nitrophenolics are removed.

In the past, one conventional treatment for removing deleterious impurities has been to contact the dinitrotoluene with an aqueous alkaline material, e.g., an alkali metal carbonate or alkali metal hydroxide and then wash with water. These alkaline materials convert by-product phenolic impurities, generally in the form of nitrocresols, to water soluble salts which then dissolve in the aqueous phase. The remaining salts and alkali are then removed from dinitrotoluene by washing with excess water.

British Pat. No. 1,031,450 is representative of the above process in that it discloses a process for separating nitrophenolics from nitroaromatics formed by the nitration of aromatic hydrocarbons with mixed acids. The basic reason given by the patentees for separating these nitrophenolic materials from product nitroaromatic is that the nitroaromatics, e.g. nitrocresols, which are formed during the nitration reaction, inhibit the reduction process. Accordingly, the nitrophenolic must be removed from the reaction product before it is further used. Two techniques for separation are disclosed. One separation technique is to wash the crude nitroaromatic compositions with sodium hydroxide or sodium carbonate. A second technique is to wash the aromatic nitro compounds with water and pass the mixture over a basic anion exchange resin which retains the nitrophenolic material.

U.S. Pat. No. 4,224,249 discloses a process for producing toluene diamine from nonwashed dinitrotoluene. One of the important features of that patent was to reduce the acid concentration in the dinitrotoluene feedstock to less than 6,000 ppm prior to reducing the nitro group to the amine. Nitrophenolic material remained with the nitrotoluene production. However, there is some objection to the high concentration of nitrophenolics in the dinitrotoluene.

SUMMARY OF THE INVENTION

This invention relates to an improvement in a process for purifying dinitrotoluene is prepared by first reacting toluene or mononitrotoluene with nitric acid in the presence of sulfuric acid, separating the crude dinitrotoluene from the resulting aqueous phases and then contacting the resultant crude dinitrotoluene with an alkaline material to form a purified dinitrotoluene product and an aqueous by-product phase. The improvement in the process relates to selectively maintaining a significant proportion of 2,4-dinitroorthocresol in the dinitrotoluene product and away from the effluent waste while permitting other nitrophenolic impurities to pass to the aqueous by-product phase or effluent waste. The improvement comprises: monitoring the pH of the aqueous phase formed during said contacting step with a pH sensitive instrument and then terminating said contacting step when the pH of the resultant aqueous phase is within a pH range of about 5.8 to 6.4.

The significant advantage of the improved process described herein is that a particular environmental offender, 2,4-dinitroorthocresol, which is formed in the mixed acid nitration of toluene, can be selectively retained with the product and essentially away from the effluent by-product while the balance of the nitrophenolics is exhausted to the effluent. Futher, the presence of the small amount of 2,4-dinitroorthocresol alone in the product dinitrotoluene does not affect any subsequent reduction reaction.

THE DRAWINGS

DETAILED DESCRIPTION OF THE INVENTION

Figure 1:
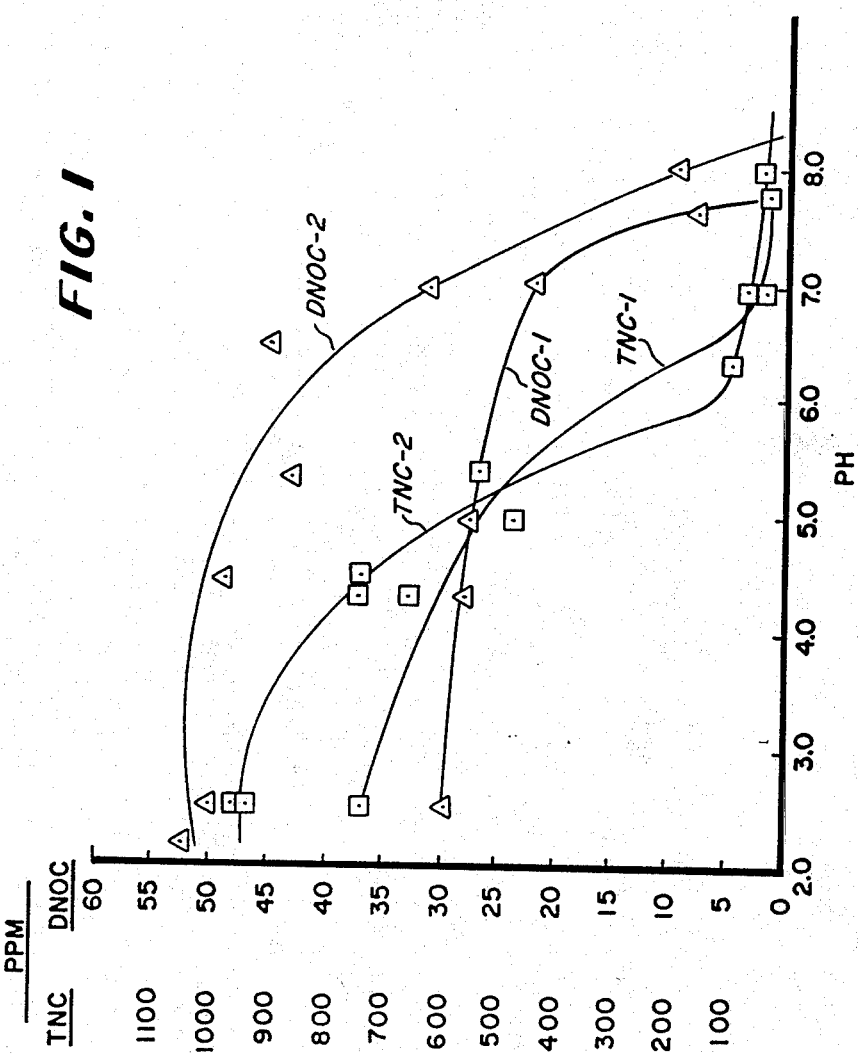
FIG. 1 is a plot of dinitrocresol and trinitrocresol content in the organic phase as a function of pH.

Dinitrotoluene which is purified according to the process of the present invention is produced by nitrating toluene using the mixed acid technique. In the mixed acid process, toluene is reacted with a mixture of nitric acid, sulfuric acid, and water under conditions effective for producing dinitrotoluene. Commercially, the nitration of toluene is conducted in a two-stage operation, the moninitration being effected in the presence of concentrated nitric acid and concentrated sulfuric acid at temperatures of about 40°–50° C. The reaction product from the first nitration zone, then, is passed to a separator where the organic phase is separated from the aqueous phase. The organic phase containing crude mononitrotoluene then is charged to a second nitration zone containing concentrated nitric acid and concentrated sulfuric acid, the dinitration being carried out at a temperature of about 60° to 80° C.

The reaction product from the dinitration zone then is removed and passed to a separator where the organic phase is separated from the aqueous phase. The key difference from the prior art processes lies in the alkaline treatment of the crude dinitrotoluene organic phase. This permits one to purify the crude dinitrotoluene, as well as the aqueous phase, for producing a product suited for reduction to toluene diamine while producing an environmentally treatable and acceptable by-product.

According to the process herein, the crude dinitrotoluene is first separated from the aqueous phase as is normally done in the past, and the crude dinitrotoluene washed or contacted with a dilute aqueous alkaline-containing solution. During washing or contacting, the pH of the resulting aqueous phase formed by the contacting step is monitored with a pH-sensitive instrument. When the pH of the system is within a range of 5.8 to 6.4, preferably 6.0–6.2, the addition of alkaline solution to the crude organic phase is terminated. The organic phase is then separated from the aqueous phase.

The purpose of the addition of alkaline material to crude dinitrotoluene is to convert the nitrophenolic materials to water soluble salts which then can be effectively removed from the dinitrotoluene product by washing with water. By monitoring the pH of the aqueous phase and terminating addition of alkaline material to the system at a pH within a range of 5.8 to 6.4, the environmentally unacceptable component, 2,4-dinitroorthocresol is maintained with the dinitrotoluene while the other nitrophenolic materials, which include picric acid and various trinitrocresols, are converted to water soluble salts. The latter are removed with the aqueous phase and are relatively easy to treat.

Any of the conventional alkaline materials used for effecting conversion of the nitrophenolic materials, particularly the cresols to water soluble salts, can be used in the practice of this invention. Examples of alkaline materials conventionally used include alkali metal hydroxides such as sodium hydroxide, ammonium hydroxide, potassium hydroxide; alkali metal carbonates and bicarbonates, e.g. sodium bicarbonate, sodium carbonate, ammonium carbonate and similar type compositions. For purposes of this invention, the ammonium ion is considered to be an alkali metal. Broadly, the solutions used for contacting the organic phase containing dinitrotoluene are aqueous solutions which contain from 0.1 to 50% by weight alkaline material and generally from about 1–10% by weight. Solutions which contain a high concentration of alkaline material are difficult to use in the contacting step because it is possible to overshoot the pH range specified for the by-product aqueous phase and thereby effect conversion of the 2,4-dinitroorthocresol to a water soluble salt. When this happens, a greater portion of the 2,4-dinitroorthocresol passes with the aqueous by-product.

The contacting temperature for maintaining 2,4-dinitroorthocresol from the aqueous phase while converting the other nitrophenolic materials to water soluble salts is within the temperature range conventionally used in the art. Typically, this temperature range is from about 60–80° C. The pressure used for the process is the same as conventionally used for effecting conversion of nitrophenolic material to water soluble salts via alkaline treatment. No significant advantages are deemed to be observed when operating at pressures greater than atmospheric pressure.

The following example is used to illustrate an embodiment of the invention.

EXAMPLE 1

Two runs of 100 ml each were made with crude dinitrotoluene obtained from a commercial dinitrotoluene unit. The dinitrotoluene had been allowed to separate from the by-product aqueous phase and then recovered. Subsequently, it was washed with water to remove traces of water soluble materials therefrom. The crude commercial product contained nitrophenolic material and had the following approximate weight percent analysis except where expressed in parts per million (ppm) by weight. The acidity level was estimated.

| Water | (4800 ppm) |
|---|---|
| Estimated Acidity as $H_2SO_4$ | 3000 ppm |

| -continued | |
|---|---|
| Cresols (ppm) | As specified in Table 1 and 2 |
| Trinitrotoluene (ppm) | 1100 |
| Nitrobenzene | 0.02 |
| Mononitrotoluene | 0.03 |
| Dinitrotoluene 2.6 | 17.5% |
| Dinitrotoluene 2.4 | 77% |
| Miscellaneous | balance |

Each 100 ml sample of crude commercial product was placed in a stirred vessel and contacted with a dilute amount of an aqueous solution of sodium carbonate, the solution being metered into the vessel. An aqueous layer formed on introduction of the sodium carbonate solution and the pH of that solution was measured. At various times during the run, samples were taken and the organic phase separated from the aqueous phase and analyzed for dinitroorthocresol content.

Tables 1 and 2 provide results for the two sets of runs and the level of cresols in the form of dinitroorthocresol (DNOC) and trinitrocresols TNC in the organic phase at each stage of the neutralization. These are designated DNC-1 and DNC-2 and TNC-1 and TNC-2 for Tables 1 and 2, respectively. The corresponding nomenclature is used for FIG. 2. In addition, the number of milliliters (ml) aqueous solution added and % sodium carbonate (calculated basis) are reported.

TABLE 1

| Run | ml | Aqueous $Na_2CO_3$ | pH | DNOC (ppm) | TNC (ppm) |
|---|---|---|---|---|---|
| Control | 0 | — | — | 29.9 | 863 |
| 1 | 28.6 | 0.302 | 2.56 | 27 | 746.9 |
| 2 | 34.7 | 0.356 | 4.32 | 26.5 | 666.9 |
| 3 | 34.8 | 0.382 | 4.98 | 27.8 | 472.4 |
| 4 | 36.0 | 0.407 | 6.89 | 22.95 | 48.5 |
| 5 | 30.75 | 0.441 | 7.68 | 8.8 | <10 |

TABLE 2

| Run | ml | Aqueous $Na_2CO_3$ | pH | DNOC (ppm) | TNC (ppm) |
|---|---|---|---|---|---|
| Control | 0 | — | — | 33.7 | 1026.2 |
| 1 | 14 | 0.25 | 2.59 | 49.9 | 975.4 |
| 2 | 10.1 | 0.5 | 4.45 | 47.8 | 753.8 |
| 3 | 9.1 | 0.5 | 5.3 | 43.9 | 528 |
| 4 | 11.5 | 0.5 | 6.34 | 46.9 | 103 |
| 5 | 9.6 | 0.5 | 6.93 | 32.0 | 50.4 |
| 6 | 11.7 | 0.5 | 8.0 | 10.5 | 53 |

Figure 2:
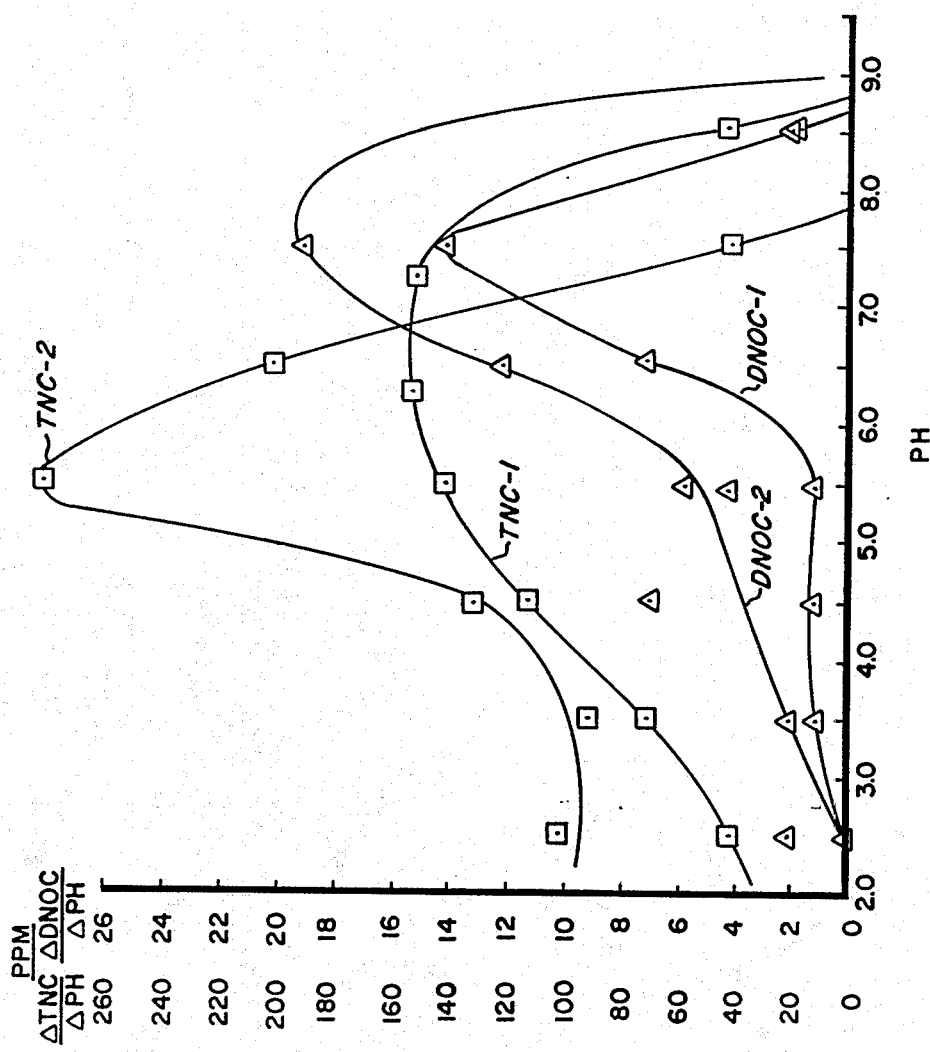
FIG. 2 represents plots of the derivative of the dinitrocresol content and trinitrocresol content taken from FIG. 1 with respect to a change in pH as a function of pH.

Tables 1 and 2 both show that the level of TNC in the organic phase falls rapidly on addition of initial amounts of sodium carbonate while the level DNOC remains substantially the same. FIG. 1 is a plot of the data for both DNOC and TNC as a function of pH from Tables 1 and 2. The curves illustrate this effect more dramatically. FIG. 2 which is a plot of the derivatives of the curves generated from the data in Tables 1 and 2, i.e., $$\frac{DNOC}{pH} \text{ vs pH and } \frac{TNC}{pH} \text{ vs pH}$$

shows that the rate of change of DNOC begins to increase rapidly at a pH of about 5.8 and extends to a pH level of about 8. The rate of change of trinitrocresol is at its highest levels at a pH of about 5.8 to 6.4 (7.5 in case 2). At a pH level of about 5.3 (Run 3 in both Tables 1 and 2), the rate of dissolution from the organic phase begins to increase but still is much slower than the rate of dissolution of the TNC. The derivatives for TNC and DNOC show that the rate of TNC dissolution is maintained at least 20 times that of DNOC during the additions, and accordingly, efficient separations are made where such rate is maintained. Further, based upon the trend established by the titration as illustrated in FIGS. 1-2, a pH of about 5.8-6.4 results in a high concentration of DNOC in the organic phase (e.g. greater than 80% by weight of the original) while the level of TNC dropped significantly (e.g. greater than 85% by weight of the original). However, even though the rate of change of TNC may be at a high level in this pH range, the actual level of DNOC in the aqueous phase generally becomes excessive at a pH value of 6.4 and above. By this technique, the overall effect of the contacting step in terms of reducing TNC and maintenance of DNOC in the organic phase is maximized.

What is claimed is:

1. In a process for preparing a purified dinitrotoluene product which comprises the steps of reacting toluene with nitric acid in the presence of sulfuric acid and then contacting the resultant crude dinitrotoluene product with an alkaline material to remove nitrocresols therefrom and thereby form a purified dinitrotoluene organic product and an aqueous by-product phase, the improvement for selectively permitting 2,4-dinitrocresol to remain with the product while removing the remainder of the nitrocresols including trinitrocresol is with the aqueous by-product, which comprises:

contacting the crude dinitrotoluene formed by the reaction of toluene with nitric acid with an alkaline material;

monitoring the contacting step with a pH-sensitive instrument;

terminating the introduction of alkaline material in the contacting step of said dinitrotoluene when the pH is within a range of from 5.8 to 6.4 and then separating the dinitrotoluene organic phase from the aqueous by product phase.

2. The process of claim 1 wherein the alkali material used for washing the dinitrotoluene is an aqueous solution of alkali metal carbonate; alkali metal bicarbonate or alkali metal hydroxide.

3. The process of claim 2 wherein the concentration of alkali metal bicarbonate, carbonate or alkali metal hydroxide in the solution is from 0.1 to 50% by weight.

4. The process of claim 3 wherein the concentration is from bicarbonate, carbonate or hydroxide of alkali metal 1-10% by weight.

5. The process of claim 4 wherein said aqueous solution contains sodium bicarbonate, sodium hydroxide or sodium carbonate.

6. In a process for purifying crude dinitrotoluene containing a mixture of nitrophenolic compounds including dinitroorthocresol and trinitroorthocresol which comprises contacting the crude dinitrotoluene with an aqueous alkali solutions in sufficient amount to convert said nitrophenolic compounds to water soluble salts and to form a distinct aqueous phase and organic phase, and then separating the resultant purified organic phase from the aqueous phase, the improvement for selectively retaining at least a major portion of dinitroorthocresol in the organic phase and at least a major portion of the trinitroorthocresol in the aqueous phase which comprises adding said aqueous alkaline solution to said crude dinitrotoluene for a time and under conditions during which the ratio of the rate of dissolution of trinitroorthocresol from the organic phase to the aqueous phase as a function of pH versus the rate of dissolution of dinitroorthocresol from the organic phase to the aqueous phase as a function of pH is at least 20:1, and the terminating said addition of aqueous alkaline solution when said ratio is less than 20:1.

* * * * *